(12) United States Patent
Schultz et al.

(10) Patent No.: US 8,552,370 B2
(45) Date of Patent: Oct. 8, 2013

(54) ROBUST STATISTICAL RECONSTRUCTION FOR CHARGED PARTICLE TOMOGRAPHY

(75) Inventors: Larry Joe Schultz, Los Alamos, NM (US); Alexei Vasilievich Klimenko, Maynard, MA (US); Andrew Mcleod Fraser, Los Alamos, NM (US); Christopher Morris, Los Alamos, NM (US); John Christopher Orum, Los Alamos, NM (US); Konstantin N. Borozdin, Los Alamos, NM (US); Michael James Sossong, Los Alamos, NM (US); Nicolas W. Hengartner, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 1734 days.

(21) Appl. No.: 11/977,409

(22) Filed: Oct. 24, 2007

(65) Prior Publication Data
US 2013/0238291 A1 Sep. 12, 2013

Related U.S. Application Data

(60) Provisional application No. 60/855,064, filed on Oct. 27, 2006.

(51) Int. Cl.
*G01N 23/201* (2006.01)
(52) U.S. Cl.
CPC ................. *G01N 23/201* (2013.01)
USPC ............ 250/306; 382/249; 382/128; 382/254
(58) Field of Classification Search
USPC .................. 250/306, 307; 382/249, 128, 254
See application file for complete search history.

(56) References Cited

U.S. PATENT DOCUMENTS

| 7,470,905 B1 | 12/2008 | Goldberg et al. | |
|---|---|---|---|
| 7,633,062 B2 * | 12/2009 | Morris et al. | 250/308 |
| 7,908,121 B2 * | 3/2011 | Green | 702/189 |
| 2006/0180753 A1 | 8/2006 | Bryman | 250/266 |
| 2007/0102648 A1 | 5/2007 | Shpantzer et al. | |

OTHER PUBLICATIONS

A Terrorist Threat—The Movement of Black Market Nuclear Materials into the United States; Gene R. Kelley, Nov. 17, 2001; www.wagingpeace.org/articles/2001/11/17_kelley_terrorist-threat.htm.
Radiographic Imaging with Cosmic-Ray Muons; K.N. Borozdin, G.E. Hogan, C. Morris, W.C. Priedhorsky, A. Saunders, L.J. Schultz, M.E. Teasdale; Los Alamos National Laboratory; vol. 422, Mar. 20, 2003, www.nature.com/nature.

(Continued)

*Primary Examiner* — Kiet T Nguyen
(74) *Attorney, Agent, or Firm* — Kermit D. Lopez; Luis M. Ortiz; Ortiz & Lopez, PLLC

(57) ABSTRACT

Systems and methods for charged particle detection including statistical reconstruction of object volume scattering density profiles from charged particle tomographic data to determine the probability distribution of charged particle scattering using a statistical multiple scattering model and determine a substantially maximum likelihood estimate of object volume scattering density using expectation maximization (ML/EM) algorithm to reconstruct the object volume scattering density. The presence of and/or type of object occupying the volume of interest can be identified from the reconstructed volume scattering density profile. The charged particle tomographic data can be cosmic ray muon tomographic data from a muon tracker for scanning packages, containers, vehicles or cargo. The method can be implemented using a computer program which is executable on a computer.

9 Claims, 16 Drawing Sheets

(56) References Cited

OTHER PUBLICATIONS

Detection of High-Z Objects Using Multiple Scattering of Cosmic Ray Muons; W.C. Priedhorsky, K.N. Borozdin, G.E. Hogan, C. Morris, A. Saunders, L.J. Schultz, M.E. Teasedale; Review of Scientific Instruments, vol. 74, No. 10, Oct. 2003.

Cosmic Ray Muon Radiography; Larry J. Schultz; Disssertation for Ph.D. Electrical and Computer Engineering, Portland State University 2003.

Image Reconstruction and Material Z Discrimination Via Cosmic Ray Muon Radiography; L.J. Schultz, K.N. Borozdin, J.J. Gomez, G.E. Hogan, J.A. McGill, C.L. Morris, W.C. Priedhorsky, A. Saunders, M.E. Teasdale; NIM Submission Draft—Jun. 30, 2003.

Convergent Incremental Optimization Transfer Algorithms: Application to Tomography; S. Ahn, J.A. Fessler, D. Blatt, A.O. Hero; IEEE Transactions of Medical Imaging, vol. 25, No. 3, Mar. 2006.

Geant4 Developments and Applications; J. Allison, K. Amako, J. Apostolakis, H. Araujo, P. Arce Dubois, M. Asai, G. Barrand, R. Capra, S. Chauvie, R. Chytracek, G.A.P. Cirrone, G. Cooperman, G. Cosmo, G. Cuttone, G.G. Daquino, M. Donszelmann, M. Dressel, G. Folger, F. Foppiano, J. Generowicz, V. Grichine, S. Guatelli, P. Gumplinger, A. Heikkinen, I. Hrivnacova, A. Howard, S. Incerti, V. Ivanchenko, T. Johnson, F. Jones, T. Koi, R. Kokoulin, M. Kossov, H. Kurashige, V. Lara, S. Larsson, F. Lei, O. Link, F. Longo, M. Maire, A. Mantero, B. Mascialino, I. McLaren, P. Mendez Lorenzo, K. Minamimoto, K. Murakami, P. Nieminen, L. Pandola, S. Parlati, L. Peralta, J. Perl, A. Pfeiffer, M.G. Pia, A. Ribon, P. Rodrigues, G. Russo, S. Sadilov, G. Santin, T. Sasaki, D. Smith N. Starkov, S. Tanaka, E. Tcherniaev, B. Tome, A. Trindade, P. Truscott, L. Urban, M. Verderi, A. Walkden, J.P. Wellisch, D. C. Willliams, D. Wright, H. Yoshida; IEEE Transactions on Nuclear Science, vol. 53, No. 1, Feb. 2006.

Maximum Likelihood from Incomplete Data Via the EM Algorithm; A.P. Dempster, N.M. Laird, D.B. Rubin; Journal of the Royal Statistical Society. Series B, vol. 39, No. 1. (1977), pp. 1-38.

Passage of Particles Through Matter; H. Bichsel, D.E. Groom, S.R. Klein; http://pdg.lbl.gov/; Aug. 29, 2007.

Statistical Image Reconstruction for Polyenergetic X-ray Computed Tomography; I.A. Elbakri, J.A. Fessler; IEEE Transactions on Medical Imaging, vol. 21, No. 2, Feb. 2002.

Optimizing the Tracking Efficiency for Cosmic Ray Muon Tomography; J. Andrew Green, C. Alexander T. Asaki, J. Bacon, G. Blampied, K. Borozdin, A. Canabal-Rey, M. Cannon, R. Chartrantd, D. Clark, C, Espinoza, E. Figueroa, A. Frazer, M. Galassi, J. Gomez, J. Gonzales, N. Hengartner, G. Hogan, A. Klimenko, P. McGaughey, G. McGregor, J. Medina, C. Morris, K. Mosher, C. Orum, F. Pazuchanics, W. Priedhorsky, A. Sanchez, A. Saunders, R. Schirato, L. Schultz, M. Sossong, M. Sottile, J. Tenbrink, R. Van de Water, K. Vixie, B. Wohlberg.

Multiple Coulomb Scattering and Spatial Resolution in Proton Radiography; U. Schneider, E. Pedroni; Med. Phys. 21 (11), Nov. 1994.

A Statistical Model for Positron Emission Tomography; Y. Vardi, L.A. Shepp, L. Kaufman; Journal of the American Statistical Association, vol. 80, No. 389. (Mar. 1985), pp. 8-20.

Borozdin, Konstantin et al., "Cosmic-Ray Muon Tomography and Its Application to the Detection of High-Z Materials", Proceedings of the 46th Annual Meeting, Institute of Nucelar Materials Management, 2005, pp. 1-8.

Van Eijik, Carl W.E., "Neutrons PSD's for the Next Generation of Spallation Neutron Sources" Nuclear Instruments and Methods in Physics Research A, 2002, vol. 477, pp. 383-390.

Zhao, T. et al. "D0 Forward—Angle Muon Tracking Detector and Its Gas System", IEEE Transactions on Nuclear Science, Jun. 2002, vol. 49, No. 3 pp. 1092-1096.

Byrd, Roger C. et al. "Nuclear Detection to Prevent or Defeat Clandestine Nuclear Attack", IEEE Sensors Journal, Aug. 2005, vol. 5, No. 4, pp. 593-609.

Zhou, Bing, "Large Precision Muon Detector for ATLAS", Nuclear Instruments and Methods in Physics Research A, 2002, vol. 494, pp. 464-473.

Hengartner, Nicolas at al., Information Extraction for Muon Radiography, Nuclear Science Symposium Conference Record, 2005 IEEE, vol. 1, Oct. 23-29, 2005, pp. 11-15.

Fessler, Jeffery A. "Statistical Methods for Image Reconstruction" (annotated slides for attendees of the NSS-MIC short Course), Oct. 24, 2004.

Schultz, L. J. et al., "Image Reconstruction and Material Z Discrimination via Cosmic Ray Muon Radiography", Nuclear Instruments and Methods in Physics Research A, 2004, vol. 519, pp. 687-694.

Jenneson, P.M. "Large Vessel Imaging Using Cosmic-ray Muons", Nuclear Instruments and Methods in Physics Research A, 2004, vol. 525, pp. 346-351.

Fessler, Jeffery A., "Penalized Maximum-Likelihood Image Reconstruction Using Space-Alternating Generalized EM Algorithms", IEEE Transactions on Image Processing, 1995, vol. 4 No. 10, pp. 1417-1429.

PCT—Notification of Transmittal of the International Search Report and the Written Opinion of the International Searching Authority, or the Declaration, Date of Mailing, Dec. 24, 2008.

\* cited by examiner

ROBUST STATISTICAL RECONSTRUCTION FOR CHARGED PARTICLE TOMOGRAPHY

CROSS-REFERENCE TO PROVISIONAL APPLICATION

This application claims priority under 35 U.S.C §119(e) to the U.S. provisional patent application No. 60/855,064, entitled "Systems, Methods and Apparatus for Particle Detection and Analysis and Field Deployment of the Same", which was filed Oct. 27, 2006, the disclosure of which is incorporated herein by reference.

STATEMENT REGARDING FEDERAL RIGHTS

This invention was made with Government support under Contract Number DE-AC52-06NA25396 awarded by the United States Department of Energy. The Government has certain rights in the invention.

TECHNICAL FIELD

Embodiments relate to fields of particle detection, analysis, control and, more particularly but not exclusively, to methods and systems for analyzing data from a charged particle detection system having a plurality of position sensitive detectors and for reconstructing the trajectory of a charged particle, such as a cosmic ray muon, passing through the charged particle detection system.

BACKGROUND

Charged particle tomography is based on the scattering of charged particles. One form of charged particle tomography is cosmic ray tomography which relies on the scattering of cosmic ray muons. Coming from deep space, stable particles, mostly protons, continuously bombard the Earth. These particles interact with atoms in the upper atmosphere to produce showers of particles that include many short-lived pions which decay and produce longer-lived muons. Muons interact with matter primarily through the Coulomb force, having no nuclear interaction and radiating much less readily than electrons. They lose energy only slowly through electromagnetic interactions. Consequently, many of the muons arrive at the Earth's surface as highly penetrating charged radiation. The muon flux at sea level is about one muon per $cm^2$ per minute.

As a muon moves through material, Coulomb scattering of the charges of subatomic particles perturb its trajectory. The total deflection depends on several material properties, but the dominant parameters are the atomic number, Z, of the nuclei and the material density.

There is a need to provide an improved method and system for reconstructing a volume of interest from muons or other charged particles passing through the volume.

BRIEF SUMMARY

The following summary of the invention is provided to facilitate an understanding of some of the technical features related to techniques, apparatus and systems for detecting particles such as charged particles like muons and statistical reconstruction of object volume scattering density profiles from charged particle tomographic data and is not intended to be a full description. A full appreciation of the various aspects of the invention can be gained by taking the entire specification, claims, drawings, and abstract as a whole.

The aforementioned aspects of the invention and other objectives and advantages can now be achieved as described herein.

According to one aspect, a detection system is described for detecting an object volume via charged particles passing through the object volume. This system includes a first set of position sensitive detectors located on a first side of an object volume to measure positions and angles of incident charged particles towards the object volume; a second set of position sensitive detectors located on a second side of the object volume opposite to the first side to measure positions and angles of outgoing charged particles exiting the object volume; and a signal processing unit to receive data of measured signals from the first set of position sensitive detectors and measured signals from the second set of position sensitive detectors. The signal processing unit processes the received data to produce a statistical reconstruction of a volume scattering density distribution within the object volume.

The signal processing unit can be configured to: (a) obtain charged particle tomographic data corresponding to scattering angles and estimated momenta of charged particles passing through an object volume; (b) provide a probability distribution of a charged particle scattering density based on a statistical multiple scattering model; (c) determine a substantially maximum likelihood estimate of the object volume scattering density using an expectation maximization (ML/EM) algorithm; and (d) output a reconstructed object volume scattering density based on the substantially maximum likelihood estimate.

According to another aspect, a method for detecting an object volume from charged particle tomographic data obtained from the object volume comprises: (a) obtaining predetermined charged particle tomographic data corresponding to scattering angles and estimated momentum of charged particles passing through object volume; (b) providing the probability distribution of charged particle scattering based on a statistical multiple scattering model; (c) determining a substantially maximum likelihood estimate of object volume scattering density using expectation maximization (ML/EM) algorithm; (d) outputting reconstructed object volume scattering density; and, if necessary, (e) making a decision based on the reconstructed object volume scattering density.

The method allows a user to identify the presence and/or type of object occupying the volume of interest from the reconstructed volume scattering density profile. Various applications include cosmic ray muon tomography for various homeland security inspection applications in which vehicles or cargo can be scanned by a muon tracker.

The charged particle tomographic data can comprise tomographic data gathered from charged particles, such as muons, generated by cosmic rays or some other source.

Making a decision based on the reconstructed object volume scattering density can comprise making a decision on at least one of (1) a presence and (2) a type of a target object in the object volume based on the reconstructed object volume scattering density.

Providing the probability distribution of a charged particle scattering for use in an expectation maximization (ML/EM) algorithm can comprise (g) obtaining a probability distribution in 2D for a charged particle based on a predefined scattering density of an homogenous object; (h) obtaining a 3D probability distribution for the charged particle based on the 2D probability distribution; (i) obtaining a probability distribution for scattering of multiple charged particles through a non-homogenous object volume characterized via basis functions; and (j) determining a probability distribution for multiple scattering based on the definition thereof and scattering and momentum measurements of the charged particles.

Obtaining the probability distribution in 2D for a charged particle based on a predefined scattering density of an homogenous object can comprise (k) determining the scattering density of a material as the expected mean square scattering of the charged particles through a unit depth of the material; (l) approximating the charged particle scattering distribution based on a Gaussian model; and (m) approximating charged particle ray scattering and displacement based on a correlated 2D Gaussian distribution.

Obtaining a 3D probability distribution for the charged particle based on the 2D probability distribution can comprise adding a coordinate and defining a three dimensional path length; computing a 3D displacement; and defining a 3D covariance matrix.

Obtaining a probability distribution for scattering of multiple charged particles through a non-homogenous object volume characterized via basis functions can comprise establishing a 3D grid of basis functions representing discrete scattering density estimates; determining the scattering/displacement covariance matrix for each individual muon as a function of the ray path and scattering density estimates; and determining a probability distribution for a plurality of charged particles as the product of individual charged particle probabilities.

Determining the substantially maximum likelihood estimate of the object volume scattering density using the expectation maximization (ML/EM) algorithm can comprise gathering measurements of scattering and momentum for each charged particle; estimating geometry of interaction of each charged particle with each basis function of the statistical scattering model; for each charged particle basis function pair, determining the weight matrix: $W_{ij}$; initializing scattering density in each basis function with a guess; and iteratively solving for the approximate maximum likelihood solution for object volume contents; wherein the iterative process is stopped at a predetermined number of iterations or when the solution is changing less than a predetermined tolerance value.

Determining a substantially maximum likelihood estimate of the object volume scattering density using the expectation maximization (ML/EM) algorithm can comprise gathering measurements of scattering and momentum for each charged particle i=1 to M $(\Delta\theta_x, \Delta\theta_y, \Delta x, \Delta_y, p_r^2)_i$; estimating the geometry of interaction of each muon with each voxel j=1 to N: $(L,T)_{ij}$; for each charged particle voxel pair, computing the weight matrix: $W_{ij}$ as $$W_{ij} = \begin{bmatrix} L_{ij} & L_{ij}^2/2 + L_{ij}T_{ij} \\ L_{ij}^2/2 + L_{ij}T_{ij} & L_{ij}^3/3 + L_{ij}^2 T_{ij} + L_{ij}T_{ij}^2 \end{bmatrix},$$

initializing a guess of the scattering density $\lambda_{j,old}$ in each voxel; and using a stopping criteria process to set $\lambda_{j,old} = \lambda_{j,new}$ for all voxels.

The expectation maximization (ML/EM) algorithm can include a mean update rule or a median update rule.

According to yet another aspect, a computed-implemented method for detecting an object volume from charged particle tomographic data obtained from the object volume comprises (a) obtaining charged particle tomographic data corresponding to scattering angles and estimated momenta of charged particles passing through an object volume; (b) providing a probability distribution of a charged particle scattering density for use in an expectation maximization (ML/EM) algorithm, the probability distribution being based on a statistical multiple scattering model; (c) determining substantially maximum likelihood estimate of object volume scattering density using the expectation maximization (ML/EM) algorithm; and (d) outputting a reconstructed object volume scattering density. A decision can be made based on the reconstructed object scattering volume density.

According to yet another aspect; a computer program product comprises a computer-usable data carrier storing instructions that, when executed by a computer, cause the computer to perform a method for statistical reconstruction of object volume density profiles from charged particle tomographic data, the method comprising: (a) obtaining predetermined charged particle tomographic data corresponding to scattering angles and estimated momenta of charged particles passing through object volume; (b) providing the probability distribution of charged particle scattering for use in an expectation maximization (ML/EM) algorithm, the probability distribution being based on a statistical multiple scattering model; (c) determining a substantially maximum likelihood estimate of object volume density using the expectation maximization (ML/EM) algorithm; and (d) outputting a reconstructed object volume scattering density.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

Figure 1:
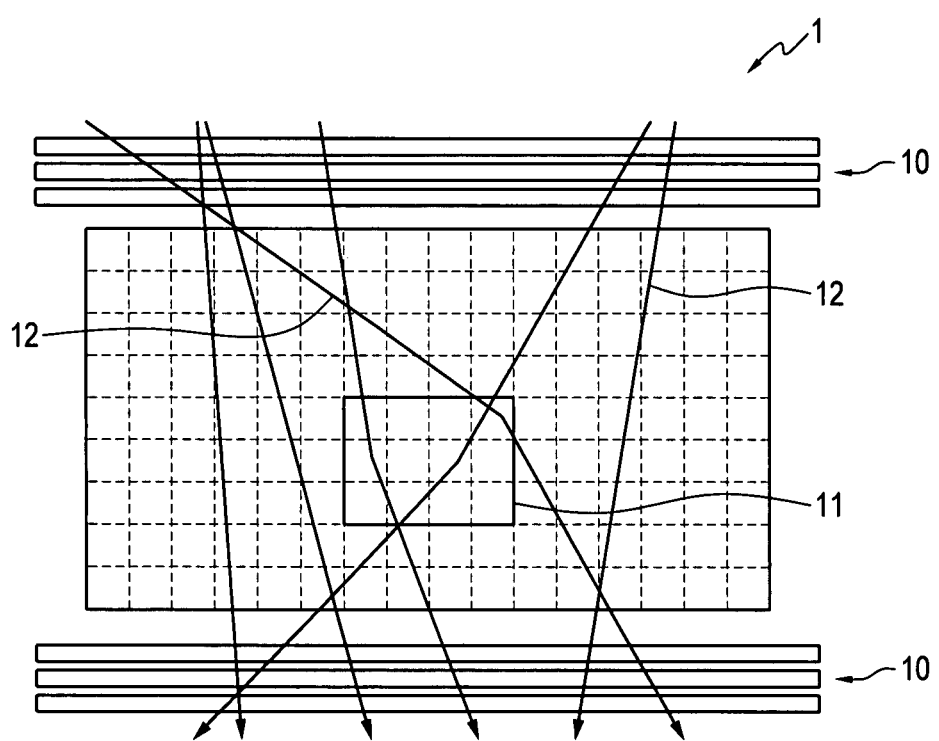
FIG. 1 illustrates one example of a muon tomography concept.

The particular values and configurations discussed in these non-limiting examples can be varied and are cited merely to illustrate at least one embodiment of the present invention and are not intended to limit the scope of the invention.

Technical features described in this application can be used to construct various particle detection systems. For example, a particle detection system for detecting muons as the charged particles can include an object holding area for placing an object to be inspected, a first set of position sensitive muon detectors located on a first side of the object holding area to measure positions and angles of incident muons towards the object holding area, a second set of position sensitive muon detectors located on a second side of the object holding area opposite to the first side to measure positions and angles of outgoing muons exiting the object holding area, and a signal processing unit, which may include, e.g., a microprocessor, to receive data of measured signals of the incoming muons from the first set of position sensitive muon detectors and measured signals of the outgoing muons from the second set of position sensitive muon detectors. As an example, each of the first and second sets of particle detectors can be implemented to include drift tubes arranged to allow at least three charged particle positional measurements in a first direction and at least three charged particle positional measurements in a second direction different from the first direction. The signal processing unit is configured to analyze scattering behaviors of the muons caused by scattering of the muons in the materials within the object holding area based on the measured incoming and outgoing positions and angles of muons to obtain a tomographic profile or the spatial distribution of scattering centers within the object holding area. The obtained tomographic profile or the spatial distribution of scattering centers can be used to reveal the presence or absence of one or more objects in the object holding area such as materials with high atomic numbers including nuclear materials or devices. Each position sensitive muon detector can be implemented in various configurations, including drift cells such as drift tubes filled with a gas which can be ionized by muons. Such a system can be used to utilize natural cosmic ray muons as the source of muons for detecting one or more objects in the object holding area.

In one implementation, the method and system for statistical reconstruction of volume scattering density profiles for charged particle tomography according to the illustrative embodiments provides an approach in which an image or model of an object can be reconstructed based on the scattering of cosmic ray charged particles moving through the object.

The trajectories are more strongly affected by special nuclear material (SNM) and materials that make good gamma ray shielding (such as lead and tungsten) than by the materials that make up more ordinary objects (such as water, plastic, aluminum, and steel). For cosmic ray charged particles, and in particular cosmic ray muons, each muon carries information about the objects that it has penetrated, and by measuring the scattering of multiple muons, one can probe the properties of these objects. In particular, one can detect high-Z objects amongst more typical low-Z and medium-Z matter.

In order to explain to explain various technical features for statistical reconstruction of volume density profiles for charged particle tomography according to the illustrative embodiments, reference will first be made to a muon tomography concept an example of which is illustrated in FIG. 1.

Sets of position sensitive detectors 10 are configured above and below an object volume 11 to be imaged to provide the positions and angles of both incoming and outgoing charged particle tracks 12 (shown by solid lines with arrows). Two or more sets of position sensitive detectors 10 arranged above a volume to be imaged provide the position and angle of incoming charged particle tracks. These detectors measure charged particle position in two orthogonal or non-orthogonal coordinates. Another set of position sensitive detectors 10 records outgoing charged particle positions and angles. Side detectors (not shown) may be used to detect more horizontally oriented charged particle tracks. The scattering angle of each charged particle track is computed from the coincident incoming and outgoing measurements. Charged particle momentum is estimated from the slight scattering occurring in the detectors themselves. or in a layer of scatterers of known properties placed between two sets of position-sensitive detector planes.

One example of a position sensitive charged particle detector is a drift tube filled with an operating gas. The drift tube can be a cylindrical tube and is filled with a detector gas such as Argon-Isobutane to enable detection of the cosmic ray charged particles, such as muons. A positive HV of about +2-3 kV is applied to a central anode wire extending along the length of the cylindrical tube with the tube exterior surface at ground so that a high-voltage static field is present. When the charged particle interacts with gas atoms, many electrons are liberated from those atoms in a straight line through a chord of the tube. The static field causes the "string" of electrons to drift toward the positively charged anode wire which is readout electronically with TDCS (time-to-digital converters) of the data acquisition electronics. Each set of detectors can be drift tubes arranged to allow at least three charged particle positional measurements in a first direction and at least three charged particle positional measurements in a second direction which is different from the first direction and may be orthogonal to the first direction.

A signal processing unit, e.g., a computer, is provided in the system in FIG. 1 to receive data of measured signals of the incoming muons by the detectors above the object volume and outgoing muons by the detectors below the object volume. This signal processing unit is configured to analyze scattering behaviors of the muons caused by scattering in the volume based on the measured incoming and outgoing positions and angles of muons to obtain a tomographic profile or the spatial distribution of scattering centers within the volume. The obtained tomographic profile or the spatial distribution of scattering centers within the volume can reveal the presence or absence of the object in the volume. In some implementations, additional drift tube detectors can be implemented on sides of the volume to form a box or four sided structure into which a package, a vehicle or cargo container can enter for scanning by the system. Thus, multiple scattering of cosmic ray muons can be used to selectively detect high z-material in a background of normal cargo. Advantageously, this technique is passive, does not deliver any radiation dose above background, and is selective to high-z dense materials. The tomographic processing part of the signal processing unit may be implemented in an on-premise computer that is at the same location with the detectors 10. Alternatively, the tomographic processing part of the signal processing unit may be implemented in a remote computer that is connected on a computer network such as a private network or a public network such as the Internet.

In the illustrative embodiment of FIG. 1, the charged particles are cosmic ray muons or other cosmic ray charged particles, and the position sensitive detectors 10 are drift cells filled with an operating gas for sensing the charged particles. Drift cells can be implemented by, for example, drift tubes with center anode wire running along the longitudinal direction of each tube. However, charged particles other than muons can be detected using position sensitive sensors other than drift cells. Furthermore, charged particles can be generated by a source other than cosmic rays. For example, muons can be generated as a low intensity beam from an accelerator.

The muons penetrating a dense object (black tracks) scatter significantly stronger than muons going through air (gray tracks). From multiple track measurements both object geometry and electron density of the material can be reconstructed. Muons passing through the volume are scattered in a manner that depends on the materials through which they pass.

The processing of measurements for cosmic ray muons in a volume under inspection (e.g., a package, a container or a vehicle) by the processing unit for the system in FIG. 1 can include reconstructing the trajectory of a muon through the volume, measuring the momentum of an incoming muon based on signals from the detectors on each side of the volume, and determining the spatial distribution of the scattering density of the volume. These and other processing results can be used to construct the tomographic profile and measure various properties of the volume such as detecting a target object.

For example, the reconstruction of the trajectory of a charged particle passing through a detectors 10 having a set of drift tubes can include (a) receiving hit signals representing identifiers of drift cells hit by charged particles and corresponding hit times; (b) grouping in-time drift cell hits identified as being associated with a track of a particular charged particle passing through the detector; (c) initially estimating time zero for the particular charged particle; (d) determining drift radii based on estimates of time zero, drift time conversion data and the time of the hit; (e) fitting linear tracks to drift radii corresponding to a particular time-zero; and (f) searching and selecting a time-zero value associated with the best of the track fits performed for particular charged particle and computing error in time-zero and tracking parameters. Such reconstruction of the track based on the time zero fit provides a reconstructed linear trajectory of the charged particle passing through the charged particle detector without having to use fast detectors (such as photomultiplier tubes with scintillator paddles) or some other fast detector which detects the passage of the muon through the apparatus to the nearest few nanoseconds to provide the time-zero.

Also for example, the processing for measuring the momentum of an incoming or outgoing muon based on signals from the detectors 10 in FIG. 1 can include, (a) configuring a plurality of position sensitive detectors to scatter a charged particle passing therethrough; (b) measuring the scattering of a charged particle in the position sensitive detectors, wherein measuring the scattering comprises obtaining at least three positional measurements of the scattering charged particle; (c) determining at least one trajectory of the charged particle from the positional measurements; and (d) determining at least one momentum measurement of the charged particle from the at least one trajectory. This technique can be used to determine the momentum of the charged particle based on the trajectory of the charged particle which is determined from the scattering of the charged particle in the position sensitive detectors themselves without the use of additional metal plates in the detector.

Details of exemplary systems and methods for statistical reconstruction of object volume scattering density profiles from charged particle tomographic data are provided below.

Figure 6:
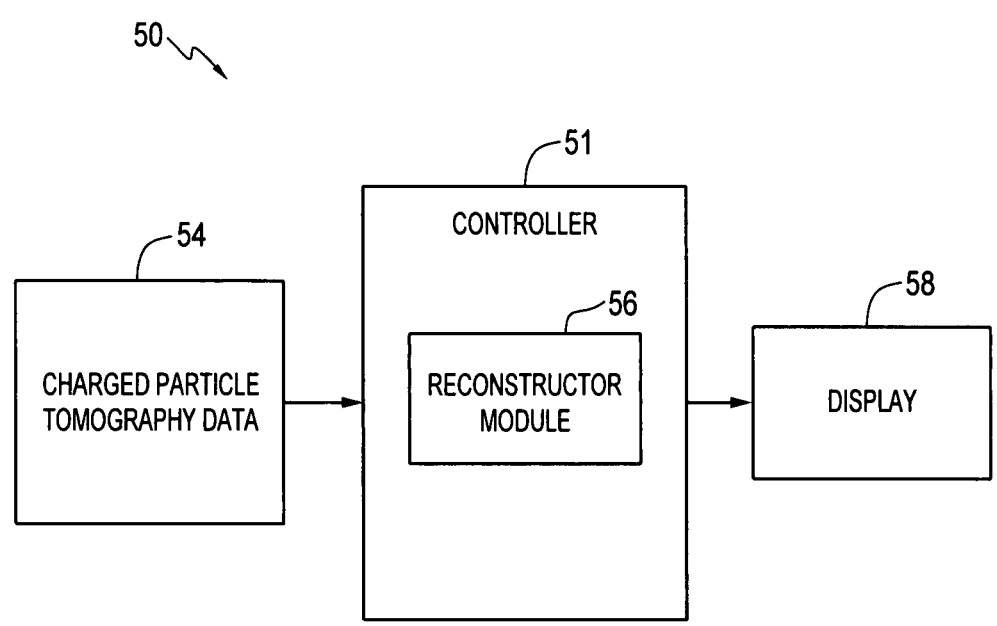
FIG. 6 illustrates an automated system for statistical reconstruction of volume scattering density profiles for muon tomography.

An example of an automated system for statistical reconstruction of volume scattering density profiles for charged particle tomography according to one embodiment is illustrated in block diagram in FIG. 6. Automated system 50 has a controller 51 adapted and arranged to receive charged particle tomographic data 54. The charged particle tomographic data can be, for example, muon tomographic data determined from measurements of the muons using the charged particle detector 1 of FIG. 1, or alternatively, any other charged particle detector having position sensitive detectors configured to enable tracking of a charged particle passing through a volume. As a result, the muon or other charged particle tomographic data can be used to extract or determine scattering angles and estimated momenta of muons or other charged particles passing through an object volume.

Automated system 50 includes a statistical reconstructor module 56 stored on the controller. Reconstructor module 56 is responsible for statistically reconstructing volume scattering density profiles for muon or other charged particle tomography. The module 56 may be implemented as a software module or a hardware module.

In the illustrative embodiment of the automated system 50 of FIG. 6, the controller 51 is formed using one or more operably linked computer processor units (CPU) based system such as a computer (PC), or other microprocessor based system such as a digital signal processor based system. The controller can be a single standard computer but in order to achieve real time results the controller typically includes a farm of parallel processing computers (not shown) sufficient in number to provide the processing capability necessary to achieve results in real-time. For example, the controller can include say 20 CPUs. The larger the scanning volume of the muon detector and the finer the desired resolution, the larger the processing computer farm will need to be.

An operating system runs on the controller 51 and may be a commercially available or open-source operating system, including but not restricted to an operating system from Apple, Windows, Linux or Unix, or others that may be developed in the future. Instructions for the operating system and applications or programs are stored in storage devices, such as a hard drive. Also, in the automated system 50, the track reconstructor module 56 is software in the form of a computer-usable data carrier storing instructions that, when executed by the controller, cause the controller to perform the method of statistical reconstructing volume scattering density profiles for charged particle tomography according to the illustrative embodiments. The module can be installed locally on the controller, as indicated in FIG. 6, or run from a remote location via a network coupled to the controller. Those skilled in the art would understand there are multiple modes of implementing such a module.

Automated system 50 also includes a display 58, operably coupled to the controller 51 for displaying to a user images or data of the object density profiles reconstructed by the system, as required. A user interface (not shown) can be operably connected to the processing system to allow a human operator to manipulate the processing system, as required.

Those skilled in the art would understand that the illustration of FIG. 6 is merely depicting one example of the embodiments of the automated system 50 and that the embodiments are not limited thereto. For example, some or all of the reconstructor module functionality can be implemented as hardware such as analogue or digital circuitry without the use of microprocessor.

Figure 15:
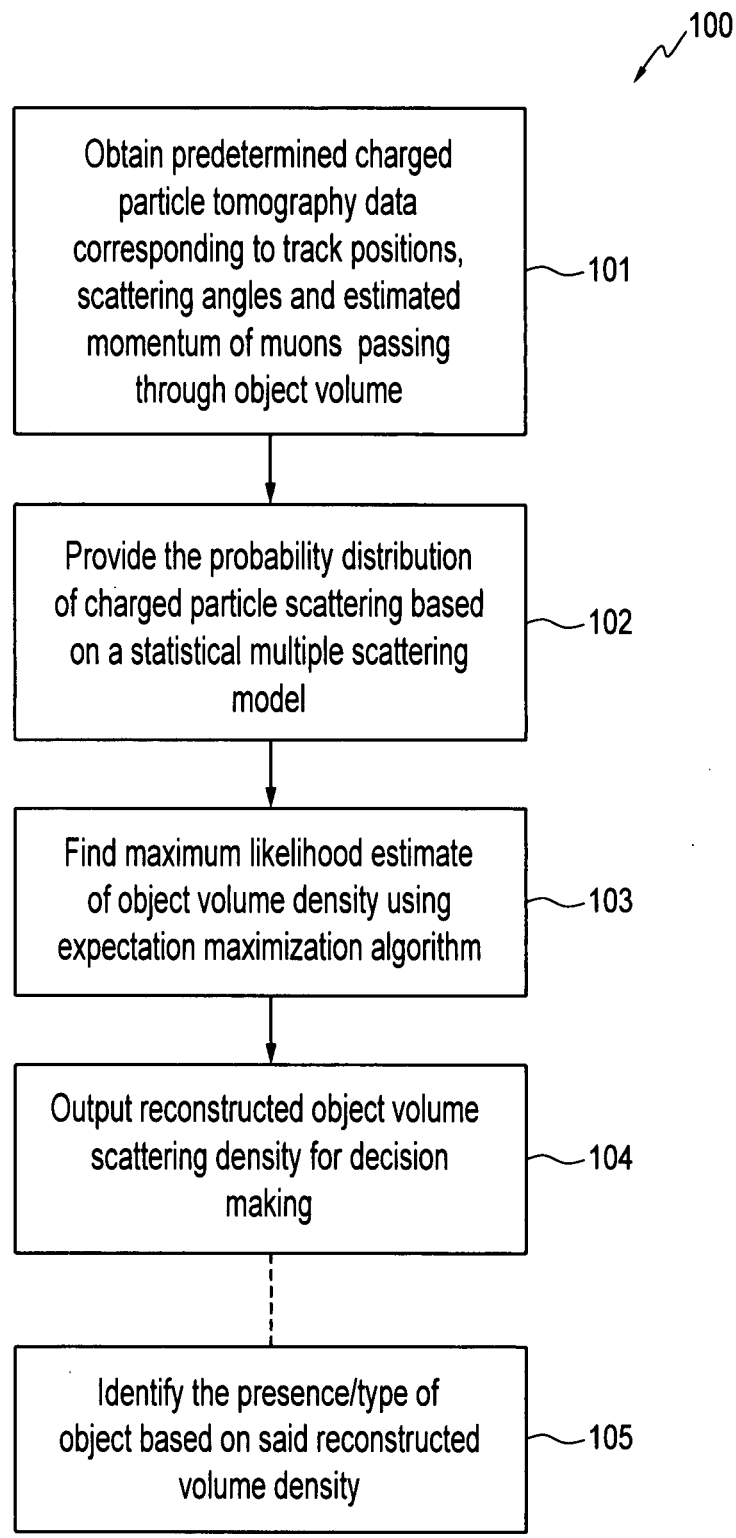
FIG. 15 illustrates a flow chart generally outlining a method for statistical reconstruction of volume scattering density profiles for charged particle tomography according to one embodiment.

Referring to FIG. 15, which illustrates a flow chart generally outlining a method for statistical reconstruction of volume density profiles for charged particle tomography according to one embodiment. Method 100 initiates by obtaining predetermined charged particle tomographic data corresponding to track positions, scattering angles and estimated momentum of charged particles passing through an object volume, as indicated in process step 101. The predetermined charged particle tomographic data can be obtained for example from the detector of FIG. 1. Thereafter, a probability distribution for scattering of a plurality of charged particles passing through object volume represented by a spatial distribution of a scattering density (to be defined below) is provided based on a multiple statistical scattering model, as indicated by the process step 102. A maximum likelihood estimate of the object volume scattering density profile is then determined using an expectation maximization algorithm, as indicated in process step 103. The reconstructed volume scattering density profile is then output for decision making (process step 104). The decision making process is optional and can be for a process of identifying the presence and/or type of object occupying the volume as indicated in process step 105. The decision making process can involve human interpretation of an image representing reconstructed density profile of the object volume and/or automated decision making by additional algorithms.

The methods and automated systems of the embodiments allow discrete tomographic reconstruction of the volume of interest to be performed based on the data provided by many charged particles. An instance of the iterative expectation maximization (EM) algorithm is used to find maximum likelihood estimates of density profiles of objects. The method and systems of the embodiments allow a user to identify the presence and/or type of object occupying the volume of interest from the reconstructed volume density profile. Various applications include cosmic ray muon tomography for various homeland security inspection applications in which vehicles or cargo can be scanned by a muon tracker. The resulting muon tomographic data can be used to reconstruct and display density profiles of the vehicles or cargo using the method and automated systems of the illustrative embodiments to allow identification of any threat objects.

Whilst maximum likelihood is used in medical image reconstructions, in particular, for PET and SPECT reconstructions, several important differences preclude use of standard methods developed for those applications. First, the measured signal—scattering angle—is stochastic, with mean equal to zero and standard deviation defined by the properties of the penetrated material. Second, cosmic-ray muons do not come from defined discrete directions, but rather have a broad, continuous angular distribution around zenith and extending nearly to the horizon. Finally, muon trajectories are not straight; it is the bending that enables us to find the rough location of a strongly scattering object. The EM algorithm is flexible and computationally efficient and its application to complex geometries can be illustrated.

Process steps 102 to 104 will now be described according to one embodiment in which the data is cosmic ray muon tomographic data obtained from the detector of FIG. 1 measuring muons passing through the volume.

Figure 15A:
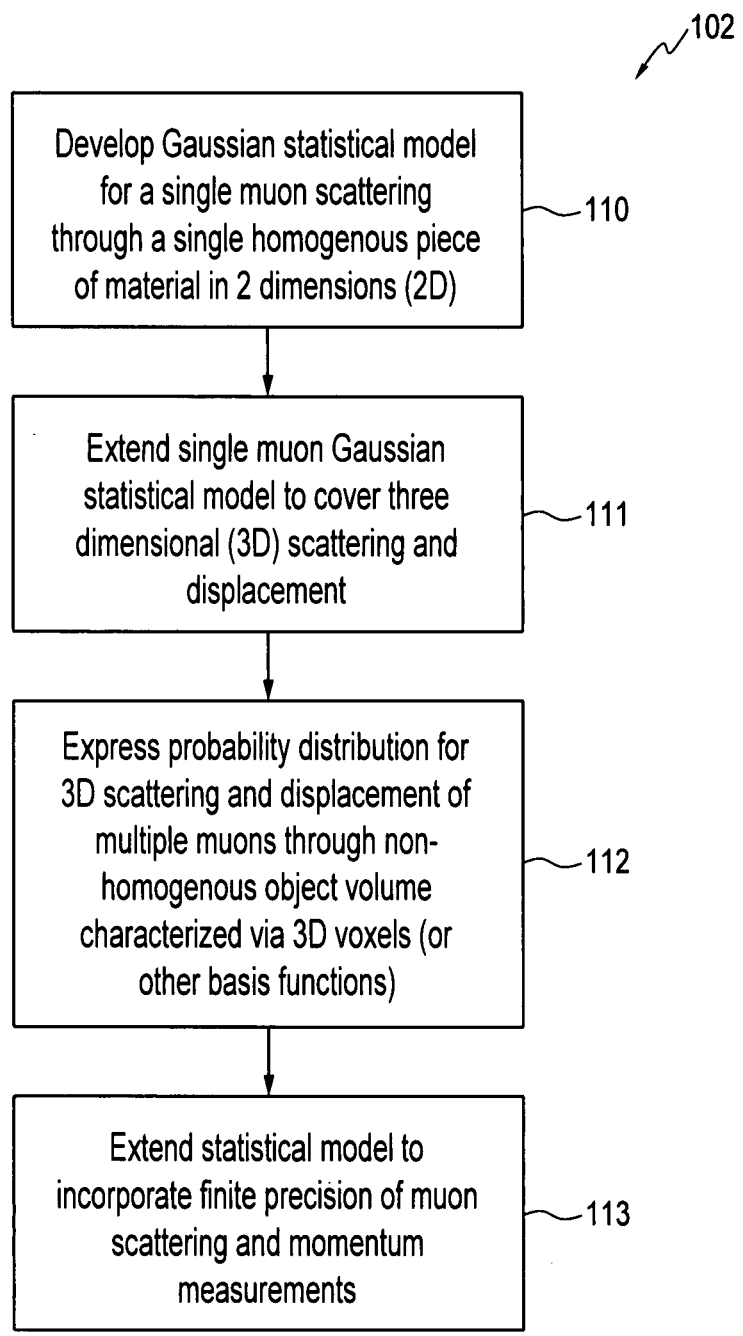
FIG. 15A illustrates a flow chart outlining an example of the process of estimating the probability distribution of scattering of a muon passing through an object volume using a multiple statistical scattering model according to one embodiment.

The process of providing the estimated probability distribution of scattering of a muon passing through an object volume using a multiple statistical scattering model (process step 102) according to one embodiment is outlined in the flow chart of FIG. 15A. As indicated in process steps 110 through 113, the process has four main components. First the probability distribution in 2D for a single muon based on a predefined scattering density of a homogenous object is estimated (process step 110). Then the 2D distribution is extended to 3D (process step 111). Next, in process step 112, a non-homogeneous object volume is expressed using voxel basis functions and the probability distribution for scattering of multiple muons given voxelized scattering density is expressed. Finally, the probability distribution expression is extended to finite precision of muon scattering and momentum measurements (process step 113).

Process steps 110 through 113 are implemented using a multiple scattering statistical model which will first be described with reference to scattering in a single layer of homogeneous material and then in a non homogenous material.

Figure 2:
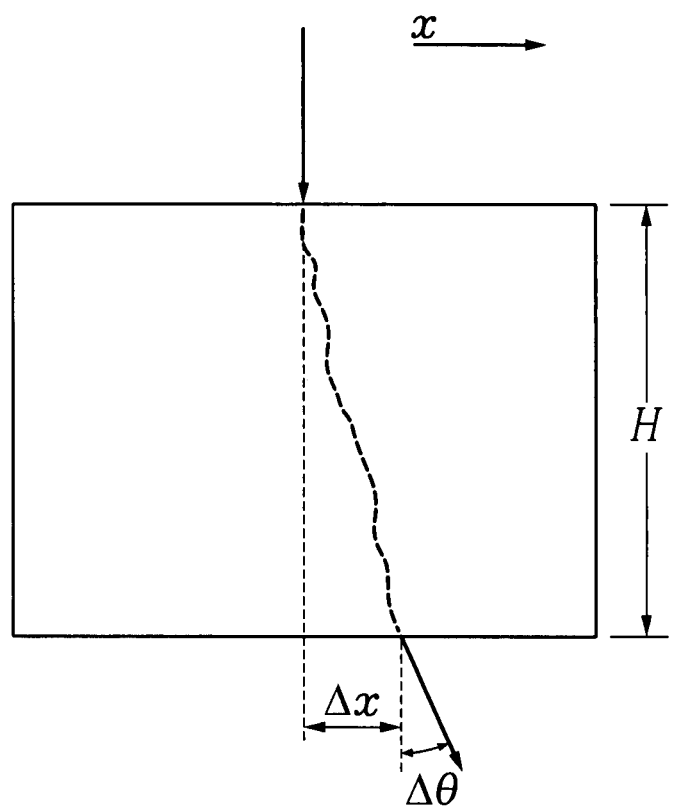
FIG. 2 illustrates a two-dimension projection of scattering and displacement used to determine Coulomb scattering.

A cosmic ray muon passing through material experiences multiple Coulomb scattering as illustrated in FIG. 2, which illustrates a two-dimensional projection of scattering and displacement used to describe multiple Coulomb scattering. In this and other figures, the magnitude of scattering is greatly exaggerated for illustrative purposes. The outgoing muon track may be characterized by the scattering angle and displacement, taken relative to the orientation and position of the incident muon. Typical scattering angles are a few tens of milliradians (1 milliradian≈0.06 degrees), and scattering angles of more than a few degrees are very uncommon. The distribution of the central 98% of scattering angles may be approximated as a zero-mean Gaussian.

$$f_{\Delta\theta}(\Delta\theta) \cong \frac{1}{\sqrt{2\pi}\,\sigma_\theta} \exp\left(-\frac{\Delta\theta^2}{2\sigma_\theta^2}\right), \qquad \text{Eq. (1)}$$

though the actual distribution has heavier or larger tails than a Gaussian. The width of the distribution may be expressed approximately in terms of material properties. Many researchers have presented empirically developed expressions for scattering as a function of various material properties, as reviewed in S. Eidelman et al., "Review of particle physics," Phys. Lett., vol. 8592, p. 1, 2004, the disclosure of which is incorporated herein by reference. A particularly simple form is $$\sigma_\theta \cong \frac{15\text{ MeV}}{\beta c p} \sqrt{\frac{H}{L_{rad}}}. \qquad \text{Eq. (2)}$$

Here, p is the particle momentum in MeV/c, H is the depth of the material, and $L_{rad}$ is the radiation length of the material, $\beta c$ is velocity (c is the speed of light), and i the approximation of β=1 is used. The radiation length decreases as atomic number and material density increase. We establish a nominal muon momentum, $p_0$, and define the scattering density of a material with radiation length $L_{rad}$ as $$\lambda(L_{rad}) \equiv \left(\frac{15}{p_0}\right)^2 \frac{1}{L_{rad}}. \qquad \text{Eq. (3)}$$

The scattering density, λ, of a material thus represents the mean square scattering angle of muons with nominal momentum passing through a unit depth of that material. Values of the scattering density in milliradian² per centimeter for some materials are about 3 for aluminum, 14 for iron, and 78 for uranium, for example. So, the variance of scattering of a muon with momentum p passing through a material with scattering density λ and depth H is $$\sigma_\theta^2 = \lambda H \left(\frac{p0}{p}\right)^2. \qquad \text{Eq. (4)}$$

Let $$p_r^2 = (p_0/p)^2, \qquad \text{Eq. (5)}$$

so $$\sigma_\theta^2 = \lambda H p_r^2. \qquad \text{Eq. (6)}$$

The displacement Δx is correlated with the scattering angle Δθ. Taken together, scattering angle and displacement provide information suggesting the position of local scattering contributors in a large volume, as suggested by the "kinks" in the paths in FIG. 1. The distribution of scattering angle and displacement may be characterized as jointly Gaussian, with zero mean and $$\sigma_{\Delta x} = \frac{H}{\sqrt{3}} \sigma_{\Delta \theta}, \qquad \text{Eq. (7)}$$

$$\rho_{\Delta \theta \Delta x} = \frac{\sqrt{3}}{2}. \qquad \text{Eq. (8)}$$

We may express the covariance matrix as $$\sum = \begin{bmatrix} \sigma_{\Delta\theta}^2 & \sigma_{\Delta\theta\Delta x} \\ \sigma_{\Delta\theta\Delta x} & \sigma_{\Delta x}^2 \end{bmatrix} = \lambda \begin{bmatrix} H & H^2/2 \\ H^2/2 & H^3/3 \end{bmatrix} p_r^2, \qquad \text{Eq. (9)}$$

$$A \equiv \begin{bmatrix} H & H^2/2 \\ H^2/2 & H^3/3 \end{bmatrix}, \qquad \text{Eq. (10)}$$

$$\sum = \lambda A p_r^2. \qquad \text{Eq. (11)}$$

Figure 15B:
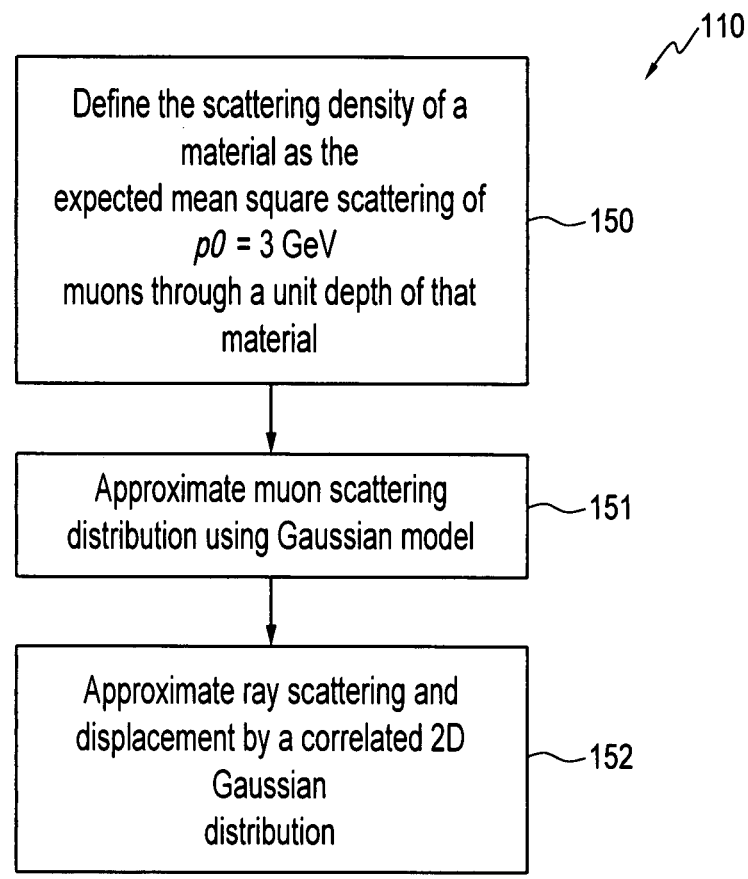
FIG. 15B illustrates a flow chart outlining an example of the process of estimating the expected probability distribution of scattering in 2D for a single muon based on a predefined scattering density of object according to one embodiment.

Having regard to the foregoing, obtaining the probability distribution of scattering in 2D for a single muon scattering (process step 110) according to one embodiment can be described as outlined in the flow chart of FIG. 15B. As indicated in process step 150, the scattering density of a material is defined as the expected mean square scattering of $p_o=3$ GeV/c muons through a unit depth of that material per Eq. (3). Then a Gaussian approximation is made for RMS scattering, as indicated in process step 151, Eqs. (1, 5, 6). Finally, a ray's scattering and displacement distribution is approximated by a zero mean correlated 2D Gaussian distribution, as indicated in process step 152, summarized via Eqs. (10, 11).

Figure 3:
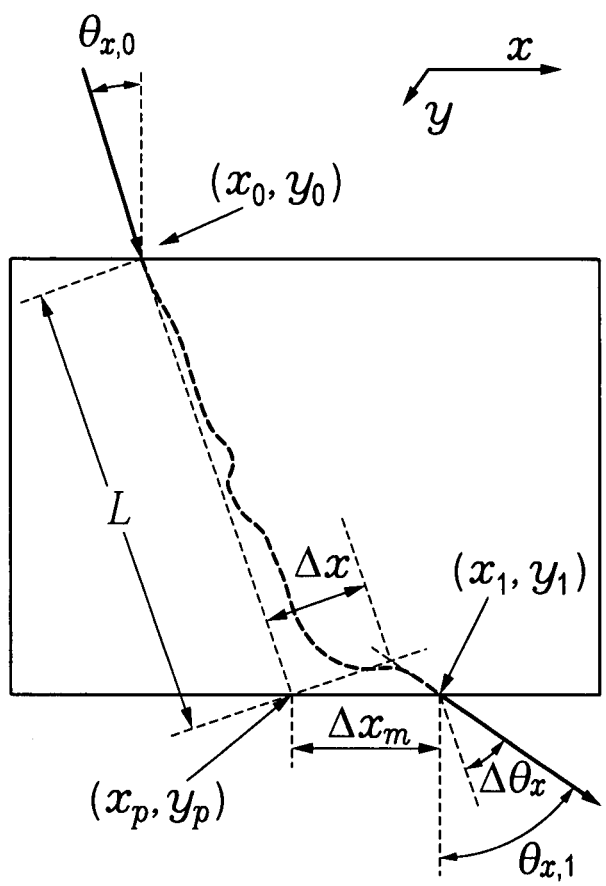
FIG. 3 illustrates the parameters of a two-dimension projection of scattering and displacement used to adjust model of 3-D scattering.

In three dimensions, scattering is characterized by considering a y coordinate orthogonal to x, and refer to scattering angles $\Delta\theta_x$ and $\Delta\theta_y$, and displacements Δx and Δy. Deflections into the x and y planes are independent and identically distributed (see Eidelman et al). The development above is based on a coordinate system which is oriented orthogonal to the direction of the incident muon. In a 3-D model we must account for 3-D path length and project displacement measurements to a plane orthogonal to the incident muon path. In FIG. 3, which illustrates parameters used to adjust model for 3-D scattering, a muon incident at a projected angle of $\theta_{x,0}$ from vertical is illustrated.

In order to assist in understanding of this 3D-scattering, it is useful to imagine the associated projected angle $\theta_{y,0}$ in an orthogonal y coordinate directed out of the page. The straight line extension of the muon path through the layer to the projected (un-scattered) point $(x_p, y_p)$ (i.e., the 3-D path length) is
is $$L = H\sqrt{1 + \tan^2\theta_{x,0} + \tan^2\theta_{y,0}} = HL_{xy}. \qquad \text{Eq. (12)}$$

Define the outgoing muon x position and angle as then let $$\delta\theta_x = \theta_{x,1} - \theta_{x,0}. \qquad \text{Eq. (13)}$$

The measured x displacement would be computed as $x_m = x_1 - x_p$, but we must rotate this measurement into the plane orthogonal to the ray path and adjust for the 3-D path length. Define displacement as $$\Delta_x = (x_1 - x_p)\cos(\theta_{x,0})L_{xy}\frac{\cos(\Delta\theta_x + \theta_{x,0})}{\cos(\Delta\theta_x)}, \qquad \text{Eq. (14)}$$

where the middle two terms account for 3-D path length and the final term projects the measurement to the proper orientation.

Finally, redefine the covariance weightings as $$A \equiv \begin{bmatrix} L & L^2/2 \\ L^2/2 & L^3/3 \end{bmatrix}. \qquad \text{Eq. (15)}$$

It is then necessary to proceed in a similar fashion for the scattering and displacement and Eq. (11) defines the covariance matrix for both and coordinate scattering. Scattering measurements are made independently in two orthogonal, horizontal coordinates. To simplify notation, we develop the analysis for only one coordinate. Combining the information from the two coordinates will be discussed later. We must note that the model is valid for "small" scattering angles and displacements. Second-order terms ignored in the derivation of the model may become significant for large angle scattering.

Figure 15C:
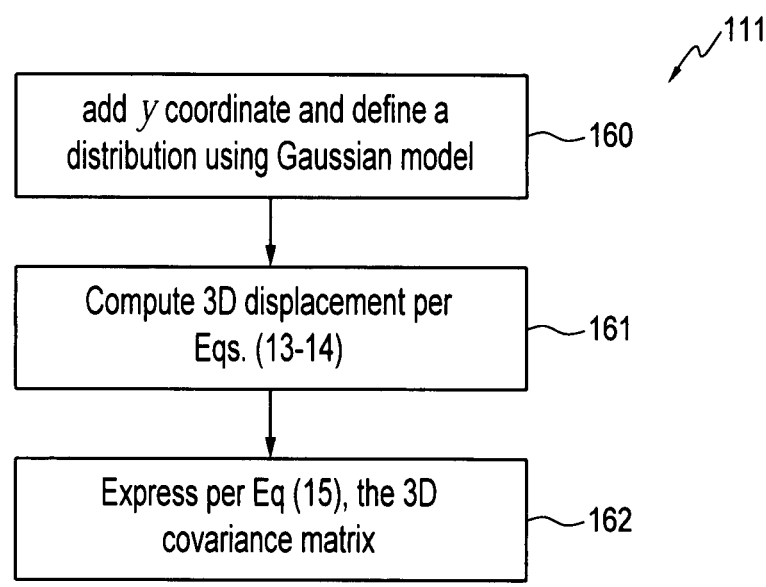
FIG. 15C illustrates a flow chart outlining an example of the process of extending the statistical model to 3D according to one embodiment.

Having regard to the foregoing, a statistical model extended to 3D is obtained (process step 111) as outlined in the flow chart of FIG. 15C according to one embodiment. First, a y coordinate is added and a three dimensional path length is defined (process step 160, Eq. (12)). Next, in process step 161, 3D displacement is computed per Eqs. (13-14). Finally, per Eq. (15), the 3D covariance matrix is expressed (process step 162).

For a non-homogeneous volume of material, the density profile is represented for purposes of reconstruction in terms of a linear combination of 3-D basis functions $\{\phi_1, \ldots, \phi_j, \phi_N\}$ with coefficients $\{v_1, \ldots, v_j, v_N\}$, i.e., $$\lambda(x, y, z) = \sum_j v_j \phi_j(x, y, z). \qquad \text{Eq. (16)}$$

Figure 4:
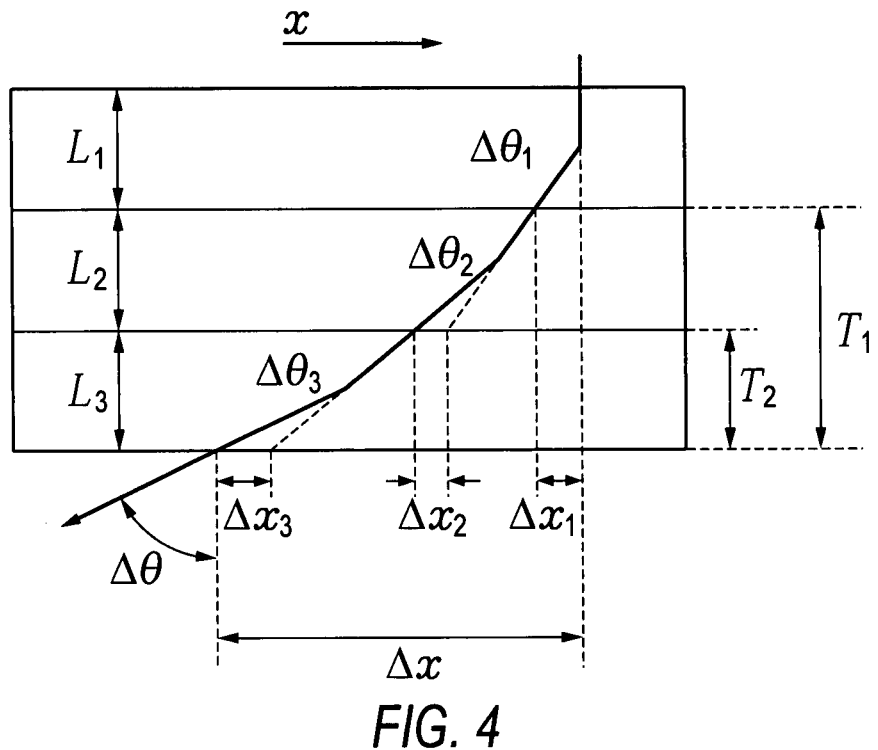
FIG. 4 illustrates scattering through multiple layers of material.

Though many choices exist for the basis functions, our attention is directed here to rectangular 3-D voxels. $\lambda_j$ is used to denote the coefficient of the $j^{th}$ basis function, i.e., the scattering density in the $j^{th}$ voxel. Considering FIG. 4, three layers (or voxels) are shown, with a ray passing through the stack, delivering observed information $\Delta\theta$ and $\Delta x$. "Hidden" scattering and displacement in the $j^{th}$ voxel are denoted $\Delta\theta_j$ and $\Delta x_j$, respectively. Again, the magnitude of scattering is exaggerated in the figure. We may relate observed to hidden data through the expressions $$\Delta\theta = \Delta\theta_1 + \Delta\theta_2 + \Delta\theta_3, \qquad \text{Eq. (17)}$$

$$\Delta x = \Delta x_1 + L_2 \tan(\Delta\theta_1) + \Delta x_2 + L_3 \tan(\Delta\theta_1 + \Delta\theta_2) + \Delta x_3 \approx \Delta x_1 + \Delta x_2 + \Delta x_3 + T_1 \Delta\theta_1 + T_2 \Delta\theta_2. \qquad \text{Eq. (18)}$$

Here, we rely on the assumption of small angle scattering in the second equation, and define $T_j$ as the 3-D ray path length from the exit point of the $j^{th}$ voxel to the exit point from the reconstruction volume. More generally, for a ray passing through a set of voxels $\aleph$, $$\Delta\theta = \sum_{j \in \aleph} \Delta\theta_j, \qquad \text{Eq. (19)}$$

$$\Delta x = \sum_{j \in \aleph} (\Delta x_j + T_j \Delta\theta_j). \qquad \text{Eq. (20)}$$

Finally, we may express the covariance of aggregate scattering/displacement for the $i^{th}$ ray by first noting that, for the $j^{th}$ voxel $$\Sigma_{ij} = \lambda_j A_{ij} p_{r,i}^2, \qquad \text{Eq. (21)}$$

where $$A_{ij} \equiv \begin{bmatrix} L_{ij} & L_{ij}^2/2 \\ L_{ij}^2/2 & L_{ij}^3/3 \end{bmatrix} \qquad \text{Eq. (22)}$$

and $L_{ij}$ is the path length of the $i^{th}$ ray through the $j^{th}$ voxel, defined to be zero for voxels not "hit" by the ray. Combining Eqs. (19)-(22), we may write $$\sum_i = p_{r,i}^2 \sum_{j \leq N} \lambda_j W_{ij}. \qquad \text{Eq. (23)}$$

Here N is the total number of voxels and we define the weight matrix $$W_{ij} \equiv \begin{bmatrix} L_{ij} & L_{ij}^2/2 + L_{ij} T_{ij} \\ L_{ij}^2/2 + L_{ij} T_{ij} & L_{ij}^3/3 + +L_{ij}^2 T_{ij} + L_{ij} T_{ij}^2 \end{bmatrix}, \qquad \text{Eq. (24)}$$

based on a simple but lengthy calculation for the elements.

Figure 5:
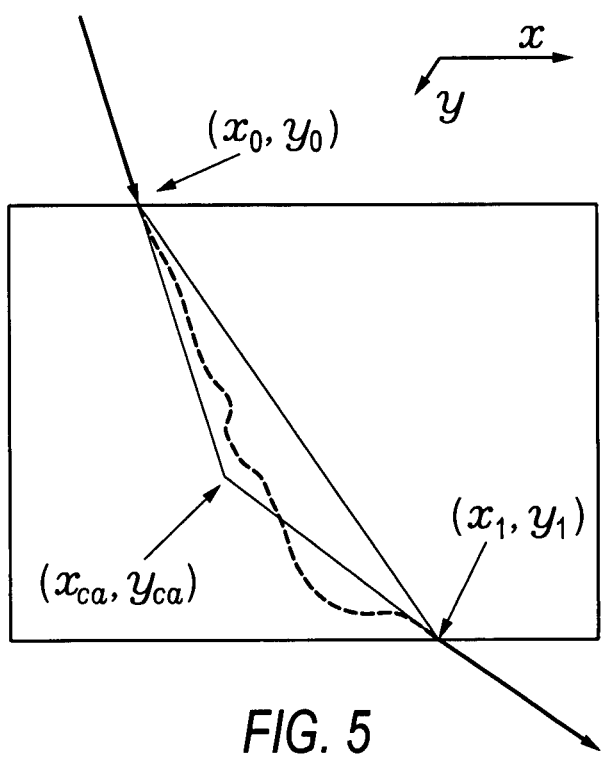
FIG. 5 illustrates using point of closest approach for path length calculations of the projection shown in FIG. 3.

Some assumption about the unknown muon path is made in order to estimate ray path lengths through voxels. Referring to FIG. 5, the approximation begins with computation of the point of closest approach (PoCA) of incoming and outgoing tracks $(x_{ca}, y_{ca})$. Then, entry to PoCA to exit points are connected to estimate voxel path lengths.

Finally, define the data vector $$D_i \equiv \begin{bmatrix} \Delta\theta_i \\ \Delta x_i \end{bmatrix} \qquad \text{Eq. (25)}$$

and let D denote all of the measurements from M muons. We write the likelihood of the data given the density profile $\lambda$ as $$P(D \mid \lambda) = \prod_{i \leq M} P(D_i \mid \lambda) \qquad \text{Eq. (26)}$$

with factors $$P(D_i \mid \lambda) = \frac{1}{2\pi |\Sigma_i|^{1/2}} \exp\left(-\frac{1}{2} D_i^T \sum_i^{-1} D_i\right). \qquad \text{Eq. (27)}$$

Figure 15D:
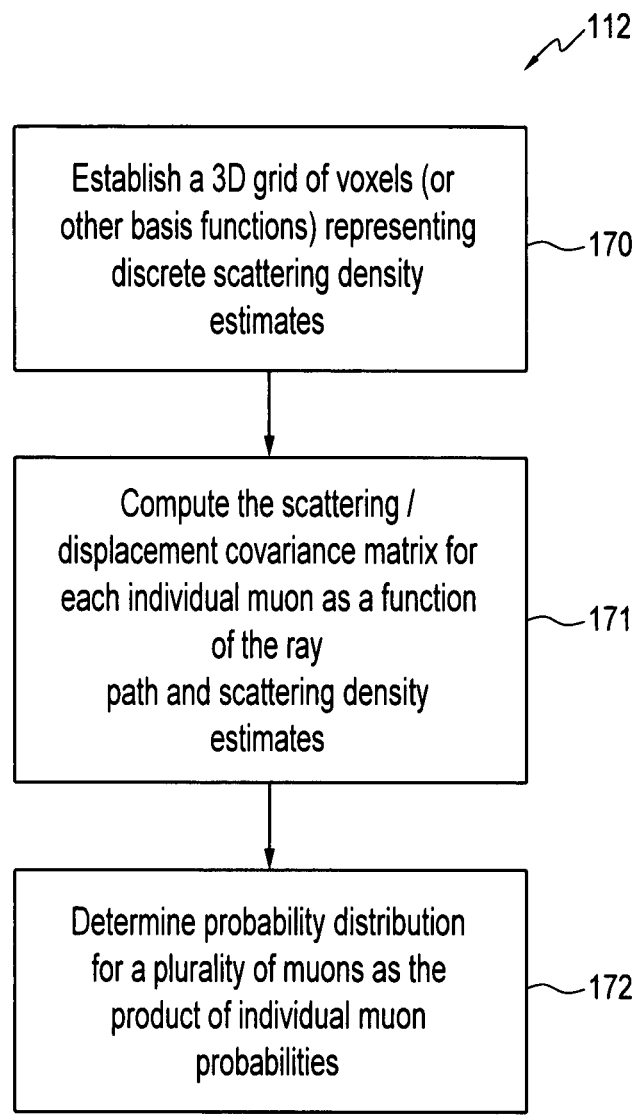
FIG. 15D illustrates a flow chart outlining an example of the process of determining the probability distribution for scattering and displacement of multiple muons through non homogenous materials according to one embodiment.

Having regard to the foregoing, a probability distribution for scattering and displacement of multiple muons through a non homogenous material can be obtained (process step 112) according to one embodiment as outlined in FIG. 15D. First a 3D grid of voxels (or other basis functions) is established (process step 170). Then in process step 171 the covariance matrix for scattering/displacement for each muon is computed, per Eqs. (23, 24). Finally the overall probability distribution for all muons, given ray paths and voxel scattering densities is computed, per Eqs. (25-27), shown as process step 172.

Having described the multiple scattering statistical model, reference will now be made to extensions of the model for experimental effects (process step 113). Real muon detectors exhibit finite position resolution. The incoming and outgoing muon tracks are characterized by angles and positions derived from track fits to multiple position measurements. Measurement errors thus propagate to the scattering angle and displacement measurements that constitute the dataset for muon tomography. The precision of a given detector is characterized by RMS error $e_p$. For a particular arrangement of detectors, the error matrix $$E \equiv \begin{bmatrix} e_{\Delta\theta}^2 & e_{\Delta\theta \Delta x} \\ e_{\Delta\theta \Delta x} & e_{\Delta x}^2 \end{bmatrix} \qquad \text{Eq. (28)}$$

may be defined based on how the error propagates. Such error is relatively easy to deal with in iterative reconstruction methods. In our case, we may account for detector error by supplementing the covariance matrix of Eq. (23)

$$\sum_i E + p_{r,i}^2 \sum_{j \leq N} (\lambda_j W_{ij}). \qquad \text{Eq. (29)}$$

In this way, noise is reduced that would otherwise appear in reconstructions due to detector error. A more accurate model for detector error should account for momentum dependency, since one source of tracking error is scattering in the detectors themselves, and scattering decreases as particle momentum increases. If an estimate of individual muon momentum, $\hat{p}_i$, is available, then the error matrix $E_i(\hat{p}_i)$ could be estimated for each ray. As is evident from Eq. (2), the width of multiple Coulomb scattering depends on the particle momentum. Different muon momentum is accounted for by introducing the factor $p_{r,i}^2$ in Eq. (5). In practice, the muon momentum is not known precisely but an estimate of the momentum of an individual muon may be estimated from measurements of scattering in a known scatterer such as the known spectrum of cosmic-ray muons. Here, it is assumed that we have a good estimate of $\hat{p}_{r,i}^2$ for each muon.

The maximum likelihood estimate of the object volume density can be determined using the expectation maximization algorithm (process step 103 of method 100). The EM algorithm relies on expressing the likelihood of the "incomplete" data in terms of the "complete" data, i.e., the observed data plus the hidden data. In our application, the observed data $D=\{D_i: 1 \leq i \leq M\}$ is the measured scattering. The hidden data $H=\{H_{ij}: 1 \leq i \leq M \;\&\; 1 \leq j \leq N\}$ is the scattering angle and displacement of the $i^{th}$ muon by the $j^{th}$ voxel. In A. Dempster, N. Laird, and D. Rubin, "Maximum likelihood from incomplete data via the EM algorithm," *J. Roy. Statist. Soc. B*, vol. 39, pp. 1-78, 1977, the disclosure of which is incorporated herein by reference, an algorithm is described in terms of the following auxiliary function:

$$Q_{DLR}=E_{H|D,\lambda^{(n)}}[\log(P(D,H|\lambda))]. \quad \text{Eq. (30)}$$

This function is the expected value of the log likelihood of both the observed and unobserved data, given the parameter vector $\lambda$ with respect to the conditional distribution of H given and the parameter vector $\lambda^{(n)}$. Each iteration of the algorithm consists of the following two steps.

E step: Estimate or characterize $P(H|D,\lambda^{(n)})$, the conditional distribution of the hidden data.

M step: Maximize the auxiliary function Q which is an expected value with respect to the distribution characterized in the E step.

In our case, since the hidden data determines the observed data uniquely, by using the simpler auxiliary function $$Q(\lambda;\lambda^{(n)})=E_{H|D,\lambda^{(n)}}[\log(P(H|\lambda))] \quad \text{Eq. (31)}$$

we obtain the same sequence of estimates $\{\lambda^{(n)}\}_{n=1}^{N_{iter}}$ that one would obtain by using $Q_{DLR}$. From the parameter estimate, $\lambda^{(n)}$, an iteration of the algorithm produces the new estimate, $\lambda^{(n+1)}$, by $$\lambda^{(n+1)}=\arg\max_\lambda(Q(\lambda;\lambda^{(n)})). \quad \text{Eq. (32)}$$

We start by noting that the probability distribution for scattering of a single muon through a single voxel follows simply from the statistical model for a single layer.

$$P(H_{ij}|\lambda) = \frac{1}{2\pi|\Sigma_{ij}|^{1/2}}\exp\left(-\frac{1}{2}H_{ij}^T \Sigma_{ij}^{-1} H_{ij}\right), \quad \text{Eq. (33)}$$

where $\tau_{ij}=\lambda_j A_{ij} p_{r,i}^2$, is defined in Eq. (21). Since the unconditional distribution of scattering in each voxel is independent of the scattering in other voxels, the probability of the aggregate set of hidden data is the product of the probability of each element. Therefore, the log likelihood may be written $$\log(P(H|\lambda)) = \sum_{j \leq N}\sum_{i: L_{ij} \neq 0}\left(-\log\lambda_j - \frac{H_{ij}^T A_{ij}^{-1} H_{ij}}{2\lambda_j p_{r,i}^2}\right) + C, \quad \text{Eq. (34)}$$

where C represents terms not containing $\lambda$. Taking the conditional expectation we write the Q function as $$Q(\lambda;\lambda^{(n)}) = C + \sum_{j \leq N} Q_j(\lambda_j;\lambda_j^{(n)}) \quad \text{Eq. (35)}$$

with summands $$Q_j(\lambda_j;\lambda_j^{(n)}) = -M_j\log\lambda_j - \frac{1}{2\lambda_j}\sum_{i:L_{ij}\neq 0} S_{ij}^{(n)}. \quad \text{Eq. (36)}$$

Here $M_j$ is the number of rays for which $L_{ij} \neq 0$ (i.e., the number of rays hitting the $j^{th}$ voxel), and $S_{ij}^{(n)}$ is defined $$S_{ij}^{(n)}=E_{H|D,\lambda^{(n)}}[p_{r,i}^{-2}H_{ij}^T A_{ij}^{-1} H_{ij}]. \quad \text{Eq. (37)}$$

Setting the derivative with respect to $\lambda_j$ of Eq. (36) to zero, we find the following iterative formula for maximizing the auxiliary function (M-step)

$$\lambda_j^{(n+1)} = \frac{1}{2M_j}\sum_{i:L_{ij}\neq 0} S_{ij}^{(n)}. \quad \text{Eq. (38)}$$

The quadratic form of $S_{ij}$ guarantees positivity of $\lambda^{(n+1)}$. It remains to calculate the conditional expectations $S_{ij}$. Let X denote the random variable $H_{ij}|D_i$. The expected value of the quadratic form $X^T A^{-1} X$ is $$E[X^T A^{-1} X] = Tr(A^{-1}\Sigma_X) + \mu_X^T A^{-1}\mu_X, \quad \text{Eq. (39)}$$

where $\mu_X$ and $\Sigma_X$ are the mean and covariance of X, respectively. Since $D_i$ depends linearly on $H_{ij}$ they are jointly Gaussian. The conditional distribution of $H_{ij}$ given $D_i$ is also Gaussian, a result from multivariate distribution theory. Using this theory and the fact that $H_{ij}$ and $D_i$ each have zero mean, we find $$\mu_X = \Sigma_{D_i H_{ij}}^T \Sigma_{D_i}^{-1} D_i, \quad \text{Eq. (40)}$$

$$\Sigma_X = \Sigma_{H_{ij}} - \Sigma_{D_i H_{ij}}^T \Sigma_{D_i}^{-1} \Sigma_{D_i H_{ij}}. \quad \text{Eq. (41)}$$

Here $\Sigma_{D_i}$, the covariance of the observed data, is given by Eq. (29), and $\Sigma_{H_{ij}}$, the covariance of the hidden data element, may be expressed via Eq. (21). Rather than writing the covariance of observed-hidden data, $\Sigma_{D_i H_{ij}}$, explicitly, we can perform a simple (though lengthy) matrix calculation to show that $$\Sigma_{D_i H_{ij}} = A_{ij}^{-1}\Sigma_{D_i H_{ij}}^T = W_{ij}(p_{r,i}^2 \lambda_j)^2. \quad \text{Eq. (42)}$$

Substituting results from Eqs. (39)-(42) into Eq. (37), we find that $$S_{ij}^{(n)} = p_{r,i}^{-2} Tr\left(A_{ij}^{-1}\sum_{H_{ij}} - A_{ij}^{-1}\sum_{D_i H_{ij}}^T \sum_{D_i}^{-1} \sum_{D_i H_{ij}}\right) + \quad \text{Eq. (43)}$$

-continued $$p_{r,i}^{-2} D_i^T \sum_{D_i}^{-1} W_{ij} \sum_{D_i}^{-1} D_i (p_{r,i}^2 \lambda_j^{(n)})^2 =$$

$$2\lambda_j^{(n)} + \left( D_i^T \sum_{D_i}^{-1} W_{ij} \sum_{D_i}^{-1} D_i - Tr\left(\sum_{D_i}^{-1} W_{ij}\right) \right) p_{r,i}^2 (\lambda_j^{(n)})^2,$$

where we have used Tr(AB)=Tr(BA) in the last step. Finally, to incorporate both x and y coordinate scattering data, we simply use the average $$S_{ij}^{(n)} = \frac{S_{ij,x}^{(n)} + S_{ij,y}^{(n)}}{2},$$  Eq. (44)

in the update Eq. (38)

t is noted that Eq. (38) represents a mean over rays hitting a voxel. Use of this equation will be termed the mean method hereafter. It will be shown below that an alternative form of this update equation is useful in reducing noise due to outlier muon data. The median method of the algorithm is defined by the altered update equation:

$$\lambda_j^{(n+1)} = \frac{1}{2} \text{median}_{i:L_{ij} \neq 0} (S_{ij}^{(n)}),$$  Eq. (45)

Figure 15E:
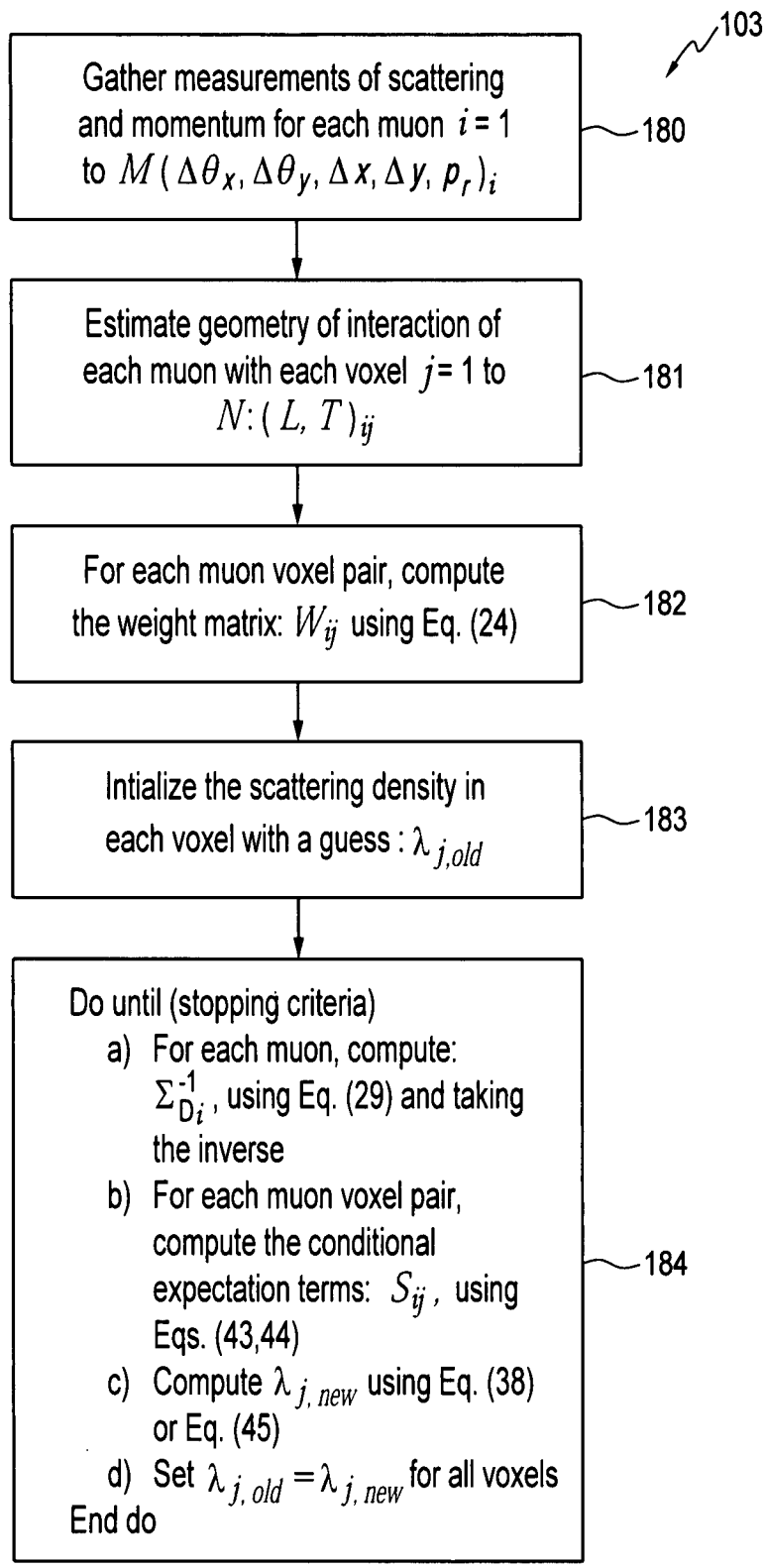
FIG. 15E illustrates a flow chart outlining an example of the process of maximizing likelihood of estimated density profiles of object volume using an expectation maximization algorithm according to one embodiment.

Having regard to the foregoing, the process of maximizing likelihood of estimated density profiles of object volume using an expectation maximization algorithm (process step 103 of method 100) is outlined in FIG. 15E. As indicated in process step 180, measurements of scattering and momentum are gathered for each muon i=1 to M ($\Delta\theta_x$, $\Delta\theta_y$, $\Delta x$, $\Delta_y$, $p_r^2$)$_i$. The geometry of interaction of each muon with each voxel j=1 to N: (L,T)$_{ij}$ is estimated (process step 181). For each muon voxel pair, the weight matrix: $W_{ij}$ is computed using Eq. (24) (process step 182). The scattering density in each voxel is initialized with a guess: $\lambda_{j,old}$ (process step 183). The stopping criteria is indicted in process step 184 as follows. For each muon, $\Sigma_D^{-1}$ is computed using Eq. (29) and the inverse taken, for each muon voxel pair, the conditional expectation terms: $S_{ij}$, are computed using Eqs. (43,44), $\lambda_{j,new}$ is computed using Eq. (38) or Eq. (45), and $\lambda_{j,old} = \lambda_{j,new}$ is set for all voxels, In order further to illustrate method 100, reference will now be made to a numerical example. A setup similar to that shown in FIG. 1 was simulated. As a first validation test, a simple simulation designed to closely match the multiple statistical scattering model was used. Single detector planes (rather than the 3 shown in the figure) were sized 2×2 m², and the vertical separation between top and bottom detectors was 1.1 m. These detectors perfectly recorded muon positions and angles. A simplified muon spectrum was used, with muons of momenta uniformly distributed from 500-10 000 MeV/c. Particles entered the volume at the upper detector plane at projected angles uniformly spanning from vertical.

Figure 7:
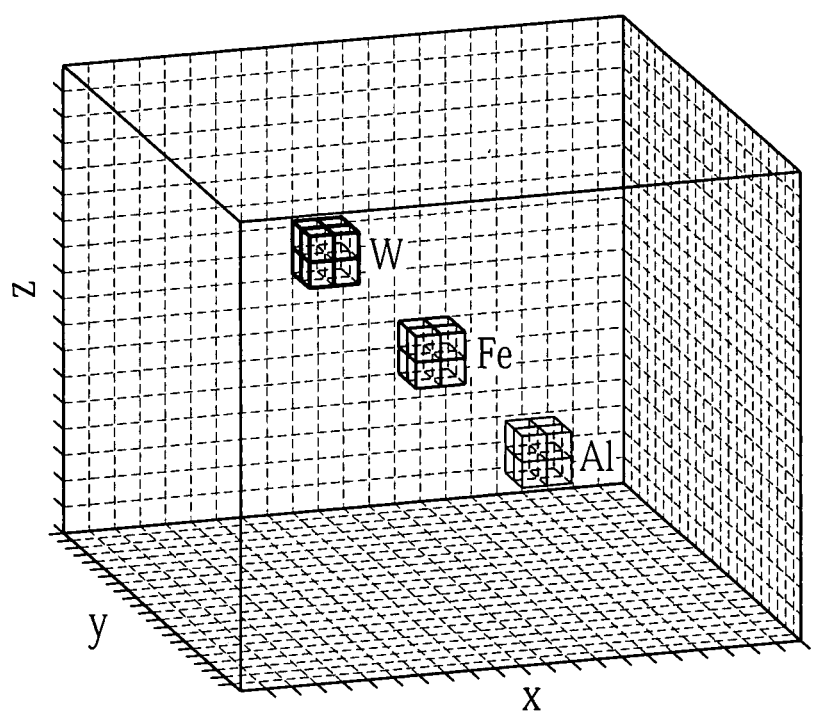
FIG. 7 illustrates a perspective view of simulated objects.
Figure 8:
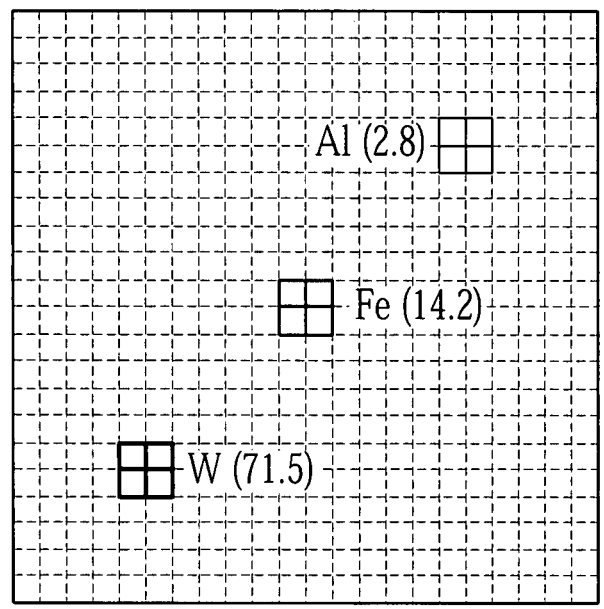
FIG. 8 illustrates overhead view of simulated objects.
Figure 9:
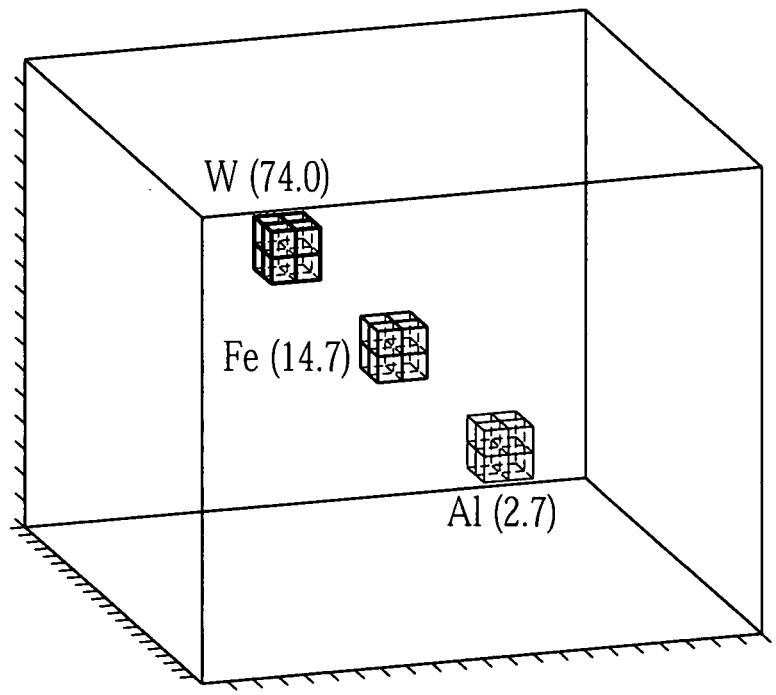
FIG. 9 illustrates reconstruction of Gaussian scattering simulation with path lengths estimated assuming two lines connected at the PoCA point.

Muon multiple scattering and displacement were simulated according to process steps 110 through 113 Objects were placed in the central 1.1×1.1×1.1 m³ portion of the volume as visualized in FIGS. 7 and 8. Three 10×10×10 cm³ cubes of materials tungsten (W), iron (Fe), and aluminum (Al), with scattering densities 71.5, 14.2, and 2.8 mrad²/cm, respectively, were simulated. The simulation assumed 400 000 muons, incident on the upper detector stack, corresponding to about 10 min of exposure. About 160 000 of these muons missed the lower detector plane, leaving 240 000 for reconstruction. A voxel size of 5×5×5 cm³ was used for reconstruction and implemented the mean method described above, assuming perfect knowledge of the momentum for each muon. The simulation started with a volume filled with air, and ran the algorithm for 100 iterations (sufficient for convergence of the block features). Results appear in FIG. 9. The averages of the reconstructed values for the 8 voxels corresponding to each of the three objects are (74.0, 14.7, 2.7) for the (W, Fe, Al) blocks, respectively. The fractional spreads (rms/mean) of the 8 voxels making up each cube are (12.6%, 13.2%, 12.1%). This result validates the inversion algorithm and implementation, given a match between simulation and inversion models.

The reconstruction appears identical to the object scene. The averages of the reconstructed values for the 8 voxels corresponding to each of the three objects are (74.0, 14.7, 2.7) for the (W, Fe, Al) blocks, respectively. The fractional spreads (rms/mean) of the 8 voxels making up each cube are (12.6%, 13.2%, 12.1%). This result validates the inversion algorithm and implementation, given a match between simulation and inversion models.

Figure 10:
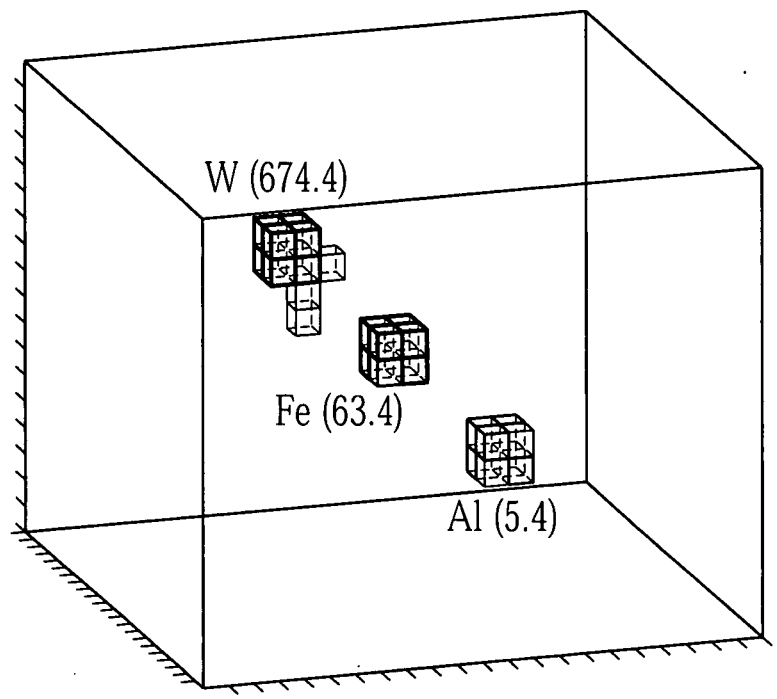
FIG. 10 illustrates reconstruction of simulated data using scattering with Non-Gaussian tails.

Next, the same scene was re-simulated using the GEANT4 Monte Carlo package. Details of GEANT4 can be found in the publication of J. Allison, "Geant4 developments and applications," *IEEE Trans. Nucl. Sci.*, vol. 53, no. 1, pp. 270-278, February 2006, the disclosure of which is incorporated herein by reference. GEANT4 implements a more complete, accurate, and validated model for multiple scattering. This model includes a more refined calculation of the width of the central Gaussian portion of the scattering distribution, implementation of the heavy tails, and the simulation of the energy loss of muons as they pass through material. A muon event generator was also used which replicated the sea-level angular and momentum distribution of cosmic ray muons. It was assumed that detectors were perfect in this simulation, with perfect knowledge of each muon's momentum, cosmic ray electrons or track secondary particles were not included. Results appear in FIG. 10. Averages of voxels values corresponding to (W, Fe, Al) blocks are (674.4, 63.4, 5.4), respectively.

The voxel values are much too high and the misclassification of several of the medium and low Z areas is apparent. Normalizing the reconstruction by dividing all voxel values by approximately 4 to produce a correct average voxel value for the medium-Z voxels does not produce correct values for high and low-Z voxels or eliminate all misclassification. The cause of this effect is a small percentage of the muons scattering in a manner not well described by the Gaussian model. The central 98% of the projected angular distribution of scattering is claimed to be well approximated as Gaussian. About 2% of all muons scatter to angles that are large relative to the statistical model described here, i.e., much larger than what would be found for a Gaussian distribution. As the square of scattering angles determine the fit, the effect can be dramatic. Muon scatterings that fall in these tails produce scattering density estimates that are too large.

Moreover, other processes such as decay of a muon within the instrument of FIG. 1 or significant detector errors may be erroneously recorded as very large angle scattering events (though these sources were not present in our simulation). This can happen anywhere in the volume, and tends to generate single voxels with unreasonably large scattering density. Such events should be eliminated because they give false-positive indications of SNM.

In order to make the EM algorithm tolerant to non-Gaussian data, the mean update rule Eq. (38) may be replaced with Eq. (45), i.e., use of the median method.

Figure 11:
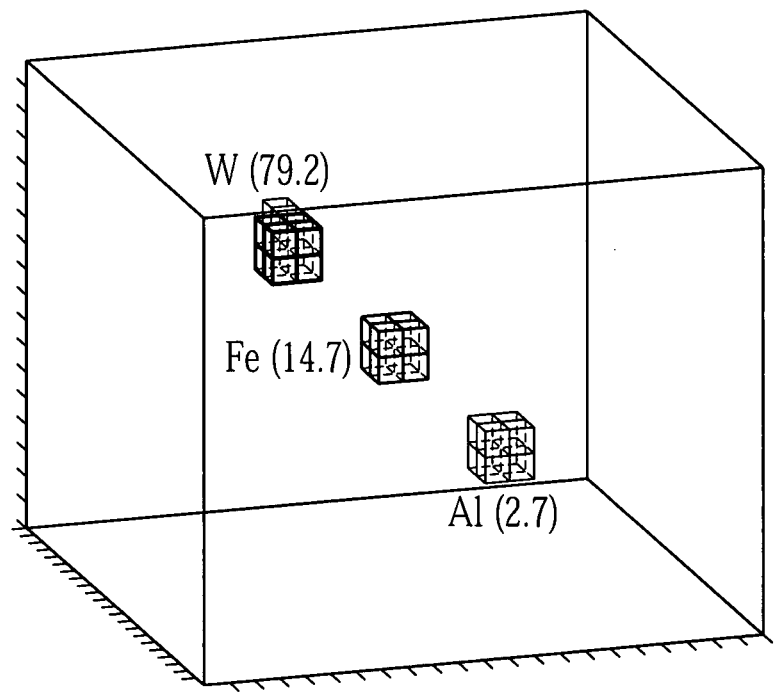
FIG. 11 illustrates reconstruction of simulated data using scattering with Non-Gaussian tails via the median method.

Results using the median method are shown in FIG. 11. Voxel averages for (W, Fe, Al) regions are (79.2, 14.2, 2.1), respectively, with fractional spreads of (21.5%, 26.3%, 23.2%). Clearly, using the median update rule improves the robustness of the inversion algorithm.

Figure 12:
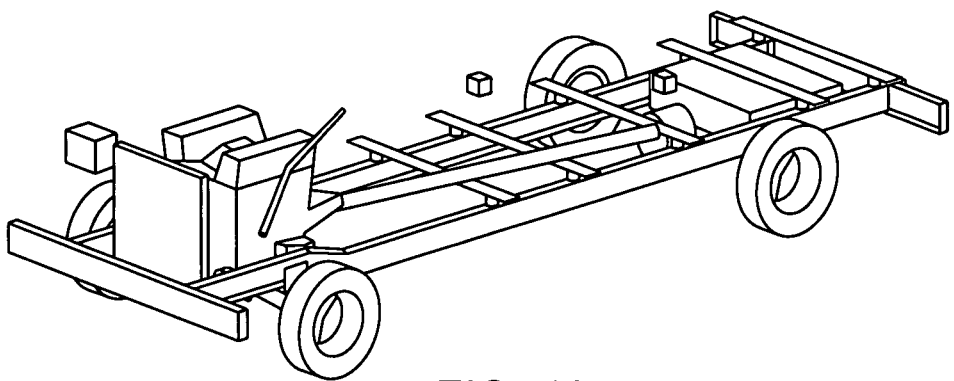
FIG. 12 illustrates major objects in a simulated passenger van.
Figure 13:
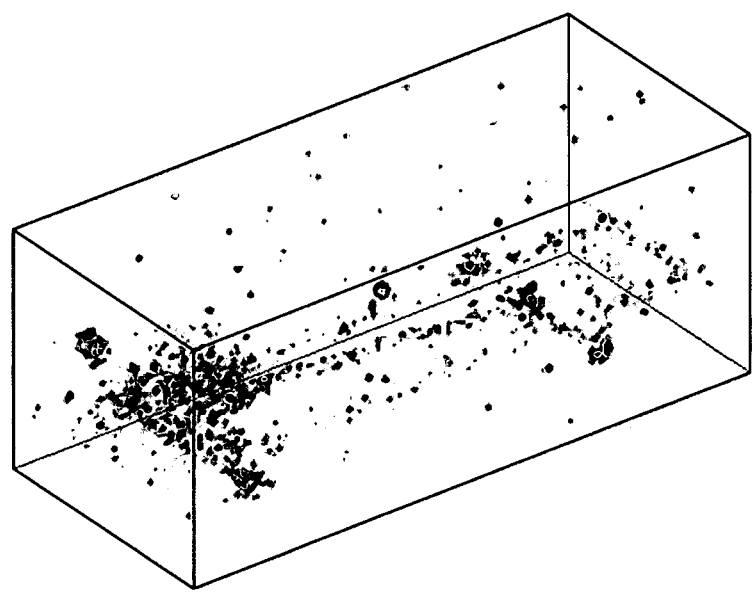
FIG. 13 illustrates reconstruction of 1 min of simulated muon exposure of the passenger van via the mean method.
Figure 14:
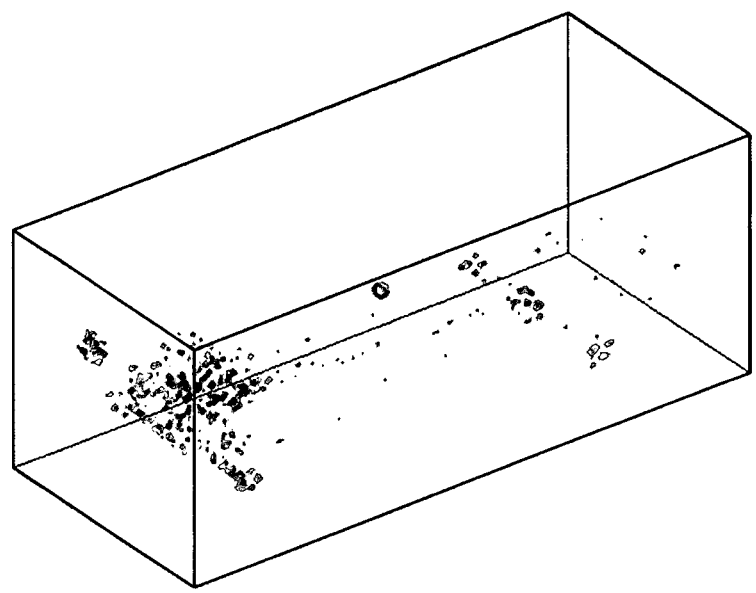
FIG. 14 illustrates reconstruction of the passenger van scene via the median method.

A more practical example of the reconstructed density profiles is shown in FIG. 12, which illustrates a detailed GEANT4 simulation of a passenger van. An illustration of the major components with the van body cut away appears in FIG. 12. The red block in the center of the illustration represents a 10×10×10 cm$^3$ solid piece of tungsten, a proxy for a high-Z threat object. In this case we used simulated detector planes located on the four long sides of the scene to take advantage of more horizontally oriented muons. 1 minute of cosmic ray muon exposure was simulated and reconstructions from the data using 5×5×5 cm$^3$ sized voxels was performed according to the mean method and the median method. FIGS. 13 and 14, respectively show visualizations of reconstructions made using mean EM method and median EM method. The effect of non-Gaussian data is quite apparent in mean method reconstruction of this scene, manifested as darker spots scattered over the image. In the median method reconstruction, these artifacts are entirely gone, and the denser components of the van (engine, battery, drive train) show up as (low-Z) or (medium-Z), while the threat object stands out darker (high-Z). The use of the median method produces results that tend to be robust against false positives resulting from non-Gaussian scattering distributions and other anomalous events.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only.

Other variations and modifications (such as regularization of the reconstruction process) of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics.

What is claimed is:

1. A detection system for detecting an object volume via charged particles passing through the object volume, comprising:
   a first set of position sensitive detectors located on a first side of an object volume to measure positions and angles of incident charged particles towards the object volume;
   a second set of position sensitive detectors located on a second side of the object volume opposite to the first side to measure positions and angles of outgoing charged particles exiting the object volume; and
   a signal processing unit to receive data of measured signals from the first set of position sensitive detectors and measured signals from the second set of position sensitive detectors, wherein the signal processing unit processes the received data to produce a statistical reconstruction of a volume scattering density distribution within the object volume.

2. The system of claim 1, wherein the signal processing unit is configured to:
   (a) obtain charged particle tomographic data corresponding to scattering angles and estimated momenta of charged particles passing through an object volume;
   (b) provide a probability distribution of a charged particle scattering density based on a statistical multiple scattering model;
   (c) determine a substantially maximum likelihood estimate of the object volume scattering density using an expectation maximization (ML/EM) algorithm; and
   (d) output a reconstructed object volume scattering density based on the substantially maximum likelihood estimate.

3. The system of claim 2, wherein the charged particles are natural cosmic ray muons incident to the object volume and the signal processing unit is configured to indicate whether a target object is present in the object volume based on the statistical reconstruction of the volume scattering density distribution within the object volume.

4. The system of claim 3, wherein:
   each of the first and second sets of particle detectors is arranged to allow at least three charged particle positional measurements in a first direction and at least three charged particle positional measurements in a second direction different from the first direction.

5. The system of claim 2, wherein the signal processing unit is further configured to:
   make a decision on at least one of (1) a presence and (2) a type of a target object in the volume based on said reconstructed object volume scattering density.

6. The system of claim 2, wherein:
   said provide a probability distribution of a charged particle scattering density based on a statistical multiple scattering model; and
   said determine a substantially maximum likelihood estimate of the object volume scattering density using an expectation maximization (ML/EM) algorithm, further comprise:
      obtain a probability distribution in 2D for a charged particle based on a predefined scattering density of a homogenous object;
      obtain a 3D probability distribution for said charged particle based on said 2D probability distribution;
      obtain a probability distribution for scattering of multiple charged particles through a non-homogenous object volume characterized via basis functions; and
      obtain a probability distribution for multiple scattering based on said definition thereof and scattering and momentum measurements of said charged particles.

7. The system of claim 6 wherein said obtain a 3D probability distribution for said charged particle based on said 2D probability distribution, further comprises:
   add a coordinate and define a three dimensional path length;
   compute a 3D displacement; and
   define a 3D covariance matrix.

8. The system of claim 2 wherein the signal processing unit is further configured to:
   establish a 3D grid of basis functions representing discrete scattering density estimates;
   determine the scattering/displacement covariance matrix for each individual moon as a function of the ray path and scattering density estimates; and determine a probability distribution for a plurality of charged particles as the product of individual charged particle probabilities.

9. The system of claim 2 wherein the signal processing unit is further configured to:

gather measurements of scattering and momentum for each cosmic ray, charged particle;

estimate geometry of interaction of each charged particle with each basis function of said statistical multiple scattering model;

for each charged particle basis function pair, determine the weight matrix: $W_{ij}$;

initialize scattering density in each basis function with a guess;

iteratively solve for the approximate maximum likelihood solution for object volume contents;

where the iterative process is stopped at a predetermined number of iterations or when the solution is changing less than a predetermined tolerance value.

* * * * *